US012479654B2

(12) United States Patent
Okudo

(10) Patent No.: US 12,479,654 B2
(45) Date of Patent: Nov. 25, 2025

(54) SURFACE MOUNT AIR DISINFECTANT/DEODORIZER HOLDER-EJECTOR DEVICE

(71) Applicant: Stephen Okudo, Suwanee, GA (US)

(72) Inventor: Stephen Okudo, Suwanee, GA (US)

( * ) Notice: Subject to any disclaimer, the term of this patent is extended or adjusted under 35 U.S.C. 154(b) by 202 days.

(21) Appl. No.: 18/076,892

(22) Filed: Dec. 7, 2022

(65) Prior Publication Data

US 2024/0190648 A1 Jun. 13, 2024

(51) Int. Cl.
*B65F 1/14* (2006.01)
*A61L 9/12* (2006.01)

(52) U.S. Cl.
CPC .................. *B65F 1/14* (2013.01); *A61L 9/12* (2013.01); *A61L 2209/15* (2013.01); *B65F 2210/129* (2013.01)

(58) Field of Classification Search
CPC ........ B65F 1/14; B65F 2210/129; A61L 9/12; A61L 2209/15
USPC ....................................................... 248/316.7
See application file for complete search history.

(56) References Cited

FOREIGN PATENT DOCUMENTS

JP 2002056600 A * 2/2002

* cited by examiner

*Primary Examiner* — Troy Chambers
(74) *Attorney, Agent, or Firm* — Bold IP, PLLC; Houda El-Jarrah

(57) ABSTRACT

Devices, systems, and methods are disclosed for facilitation of continuous release of fluids or vaporizable solids using disinfectants, deodorizers, repellants, etc., into an enclosed unit, such as trash-can in consistent and predictable amounts. The device generally includes a surface mount holder-ejector device in the resemblance of letter "H"; inward slanted upper arm as in the upper arm of letter "H"; inward slanted lower arm as in lower arm of letter "H"; or slightly curve bilateral arms as in letter "H" that may have thumb-finger fitting. The device has an encasement unit with holder-ejection mechanism mounted on the horizontal arm of the device as in the horizontal arm of letter "H". Device can be utilized with modified disposable or refillable fluid container cartridge adaptable to the device, and device surface wall affixer. The lower "H" shaped arms of the device may be thumb-finger compressed to cause outward pull of the two upper "H" shaped arms of the device to allow insertion or ejection process of the cartridge. The ends of the two upper arms of the device have inward projection forming stoppers/internal grip surface that causes retention of the cartridge in the device and restricting outward pressure by the spring and flat-plate beneath the cartridge.

7 Claims, 18 Drawing Sheets

Side view of flanged-top encasement

Front view (10/20)

Side view (10),(20),( 50 ),&(31)

Front view (10/12)

Side view (10),(20),
( 50 ),&(30)

SURFACE MOUNT AIR DISINFECTANT/DEODORIZER HOLDER-EJECTOR DEVICE

CROSS-REFERENCE TO RELATED APPLICATIONS

Not Applicable

FIELD OF THE INVENTION

The present disclosure relates to surface mount air freshener/disinfectant/deodorizer holder-ejector device in particular; to maintain retention of the device, retention of the device adapted air-conditioning product container, and overall device operation air freshening/disinfecting/deodorizing while mounted onto a movable lead of an enclosable unit.

BACKGROUND

Trash-can sanitization has been a continuing challenge for essentially as long as there had been trash-can containers. Over the years, many different techniques and devices have been developed, particularly for trash-can sanitization and odor control. Some of the challenges include maintaining continuous dissemination of disinfectant/deodorizer and retainment of device during removal-replacement of trash-bag or emptying of trash-can. The present invention is typically made of plastic material, remains reusable, allows for product replacement with minimal user exposure to contamination.

Despite the many different techniques and devices that have been developed, there is a continuing long felt need in the industry for improved trashcan disinfecting/deodorizing device and methods.

BRIEF SUMMARY OF THE INVENTION

Accordingly, the present invention provides devices and method for disinfecting/deodorizing an enclosed unit, such as disinfecting/deodorizing trash-can container using; one or more of disinfectants, deodorizers, insect repellants, etc., in an enclosed unit, such as trash-can, in consistent and controlled amounts. Devices generally include a holding and ejecting mechanism to keep in place dispensation of disinfectants, deodorizers, insect repellants, etc. into the enclosed unit and for the release of product container after product finish while remain in place for device reuse.

In various embodiments, the device may include a disposable or refillable cartridge and device surface wall affixer. 1) Device may have the resemblance of letter "H"; inward slanted upper a rm of letter "H"; inward slanted lower arm of letter "H"; or slightly curve bilateral arms of letter "H", such that any of these configurations may be thumb-finger fitting. 2) The lower "H" shaped arms of the device may be thumb-finger compressible to cause outward pull of the two upper "H" shaped arms of the device. 3) The ends of the two upper arms of the device have inward projection forming stoppers or grip internal surface that are opposite in direction at rest position. 4) A top-flanged cup fitted on the horizontal beam connecting the two vertical arms of the device. 5) Out-stretched spring fitted to the interior center base of the top-flanged cup that suspends a flat-plate which may freely move in the cup but restricted by the cup flange. 6) Inverted letter "L" shaped cup holder attached to flanged cup and may be located on the cup-side perpendicular to the side of the two letter "H" shaped arms of the device. 7) A hollow cubic/cuboid surface affixable cup holder into which top-flanged cup holder is placed to secure device to the interior surface wall of the enclosed unit.

BRIEF DESCRIPTION OF THE DRAWINGS

The accompanying drawings are included for the purpose of exemplary illustration of various aspects of the present invention to aid in description, and not for purposes of limiting the invention, wherein.

Figure 1A:
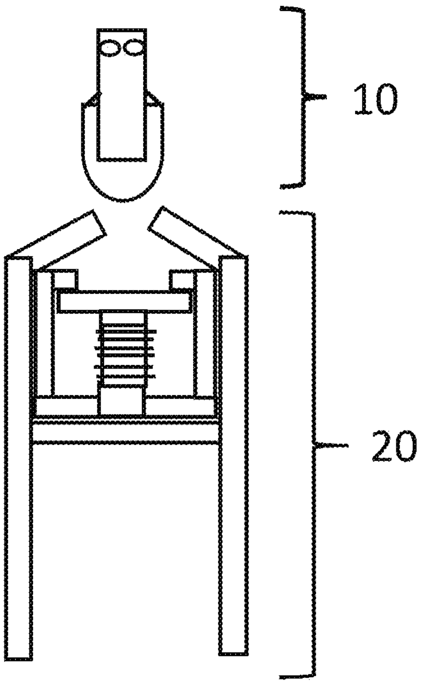
FIG. 1A illustrates an assembly view of an air disinfectant holder-ejector device and air disinfectant cartridge.

In the drawings and detailed description, the same or similar reference numbers may identify the same or similar elements. It will be appreciated that the implementations, features, etc. described with respect to embodiments in specific figures may be implemented with respect to other embodiments in other figures, unless expressly stated, or otherwise not possible.

DETAILED DESCRIPTION OF THE INVENTION

Figure 1B:
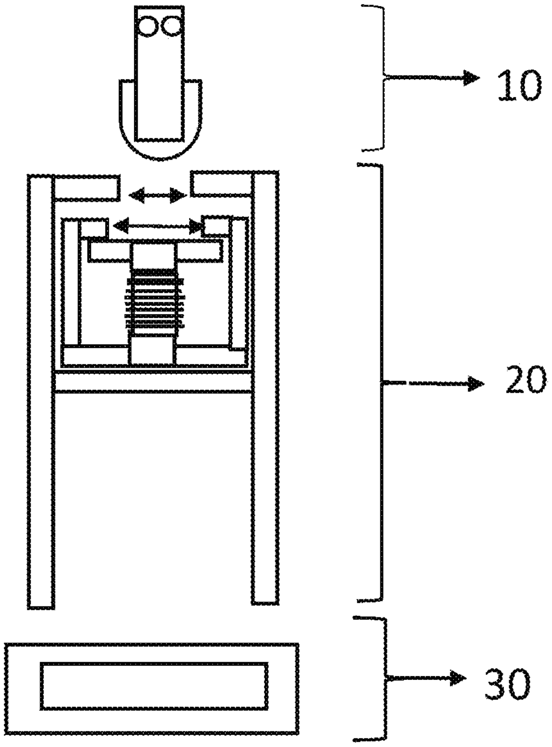
FIG. 1B illustrates an assembly view of the air disinfectant holder-ejector device and air disinfectant cartridge in FIG. 1A along with a surface affixable cup holder.
Figure 1C:
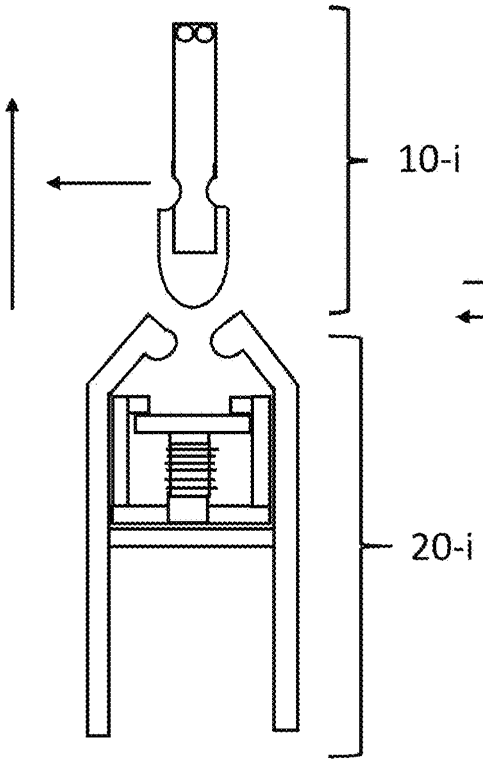
FIG. 1C illustrates another embodiment of an air disinfectant holder-ejector device having slanted stopper arms and an air disinfectant cartridge having a different exemplary shape.
Figure 1D:
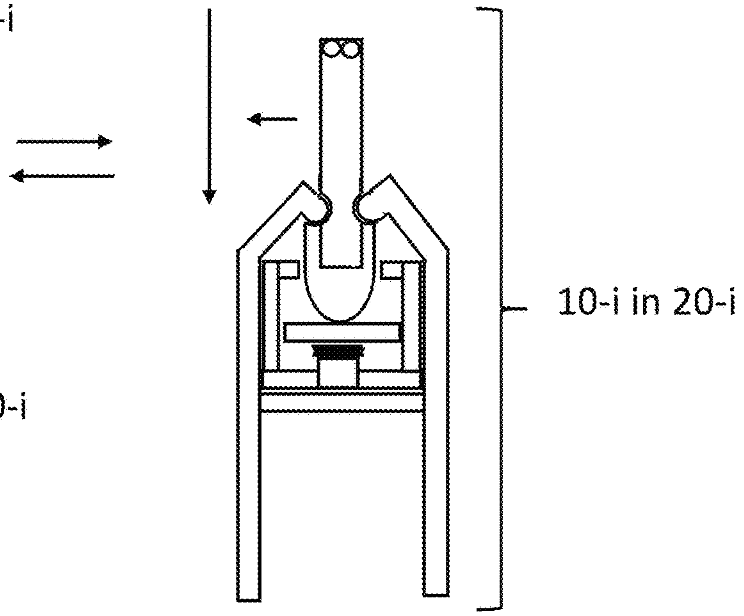
FIG. 1D illustrates a cross-sectional view of the air disinfectant cartridge shown in FIG. 1C inserted into the air disinfectant holder-ejector device and the slanted stopper arms holding the air disinfectant cartridge in place.
Figure 2A:
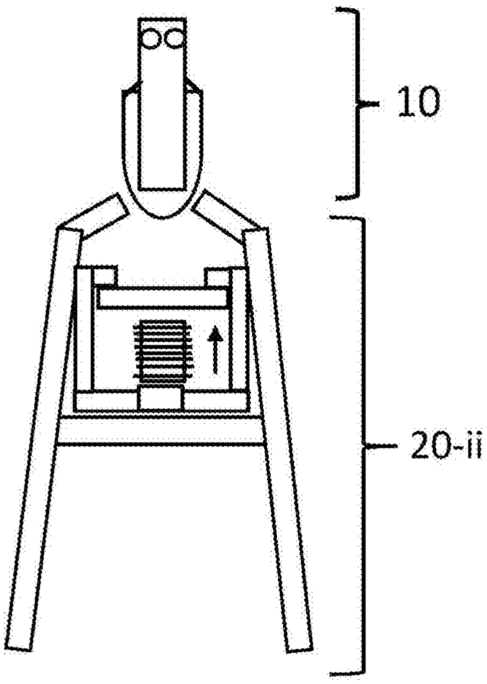
FIG. 2A shows an exemplary view of the air disinfectant holder-ejector device shown in FIG. 1A with a compressible spring retracted and the arms of the air disinfectant holder-ejector device in an initial slanted position.
Figure 2B:
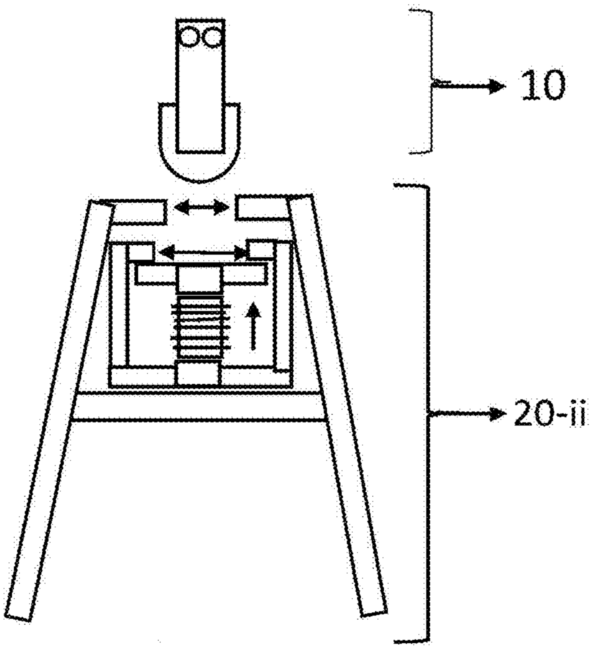
FIG. 2B shows an exemplary view of the air disinfectant holder-ejector device shown in FIG. 2B with the compressible spring in a fully raised position and the arms of the device in an expanded position.

FIG. 1A, FIG. 1B, FIG. 1C, FIG. 1D, FIG. 2A, and FIG. 2B, including respective sub-figures illustrates a cross-sectional front view of exemplary embodiments of the device in various neutral positions. FIG. 1A and FIG. 1B illustrate a cross sectional side view of the air disinfectant holder-ejector device 20, a surface affixable cup holder 30; and a device cartridge 10 as shown.

Figure 4:
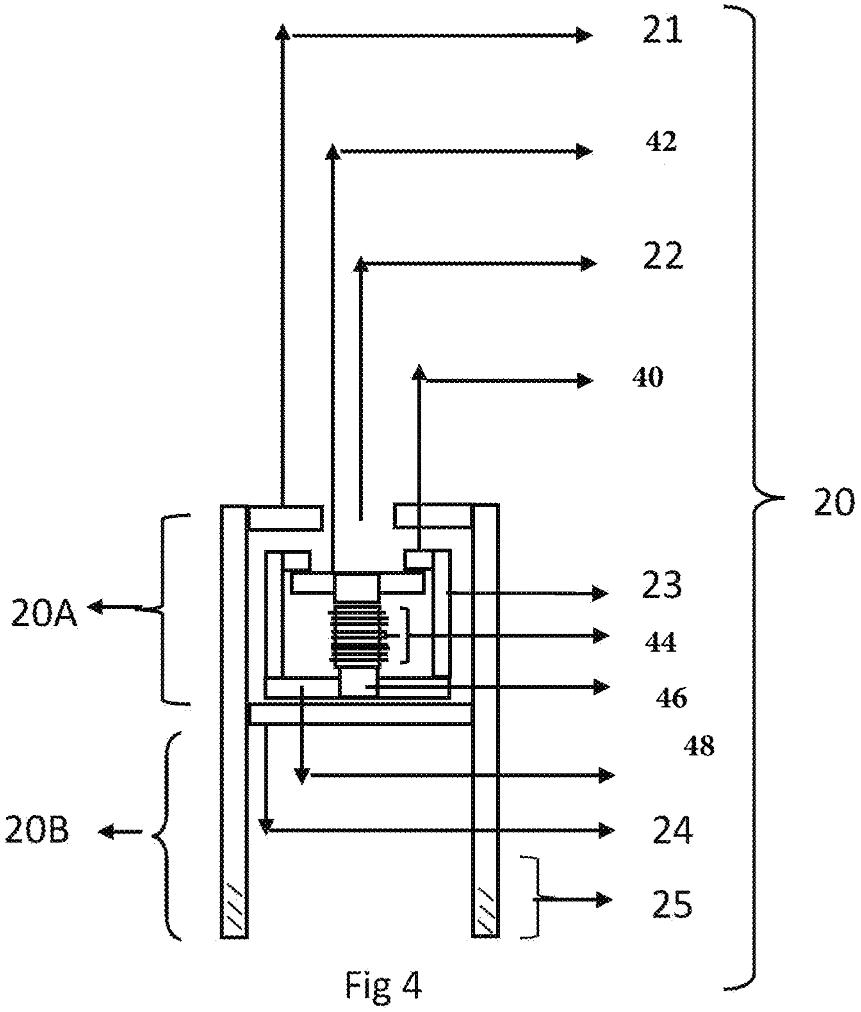
FIG. 4 shows an assembly view of the air disinfectant holder-ejector device in a neutral position with a top flanged cup inserted within the device.

FIG. 4. illustrates a cross-sectional frontal view of exemplary embodiments of the air disinfectant holder-ejector device 10 in a neutral position with numeral identification.

Figure 5:
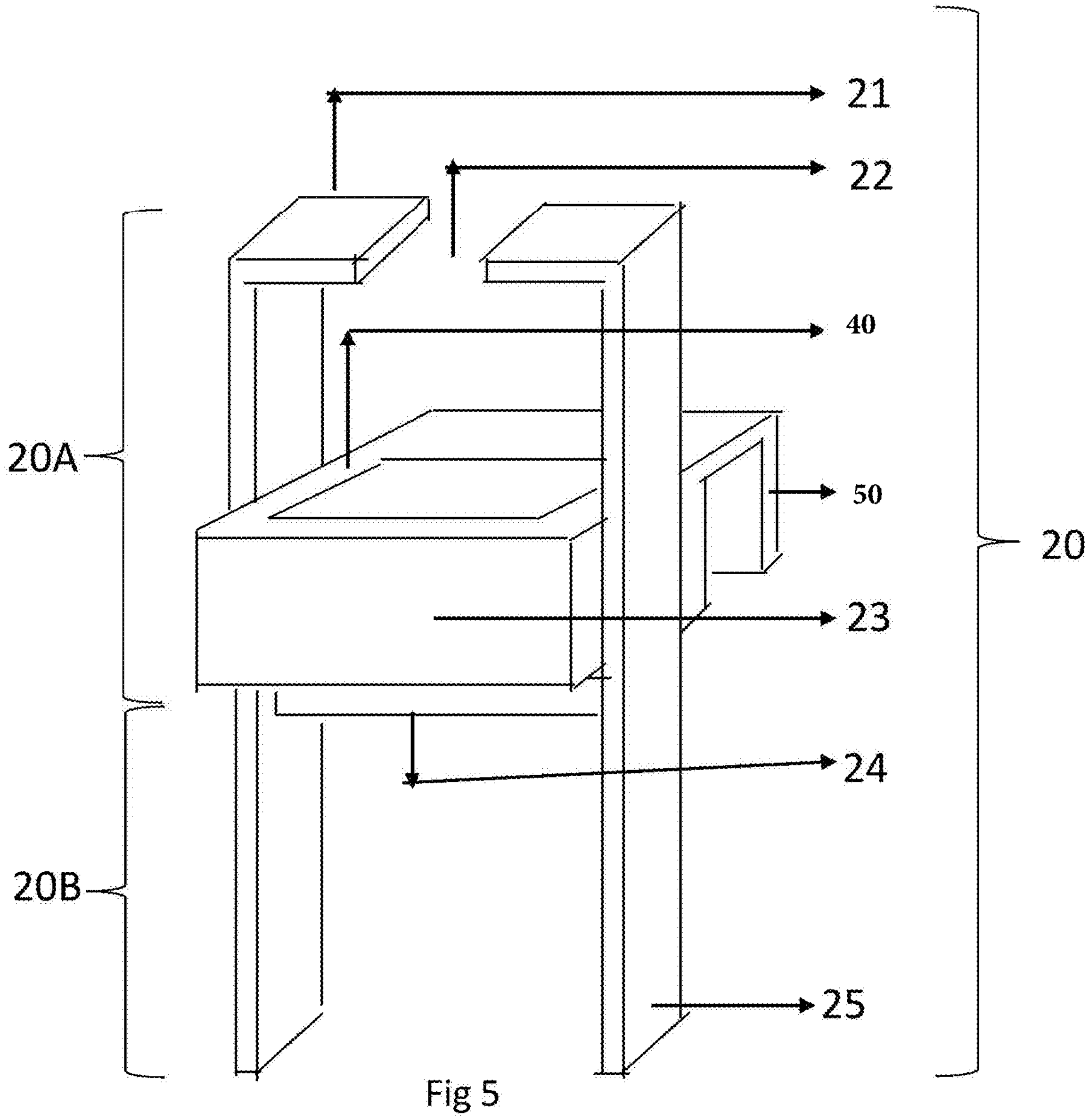
FIG. 5 shows a three dimensional view of the air disinfectant holder-ejector device of FIG. 1A with a top-flanged cup held in place.

FIG. 5. illustrates a three-dimensional view of exemplary embodiments of the device in a neutral position with numeral identification and description of component parts. As shown in FIG. 5, device 20 component description is as follows: 20A is the device upper arms with stopper/grip projections 21; 20B is the device lower arms with end part 25; 22 is the space between the stoppers; 23 is the device top-flanged cup; and 24 is the device horizontal arms connecting vertical arms to give the appearance of letter "H".

Figure 6A:
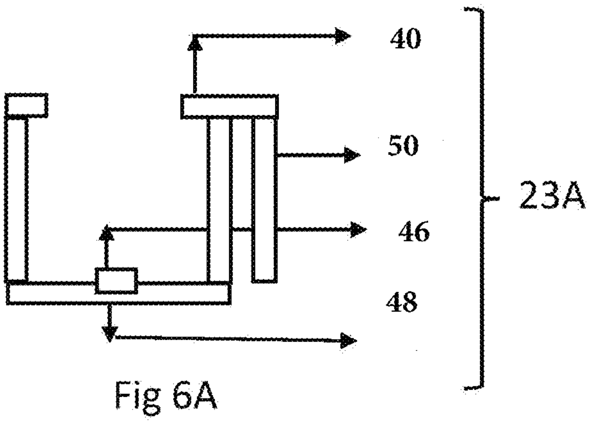
FIG. 6A illustrates a view of a top-flanged cup.
Figure 6B:
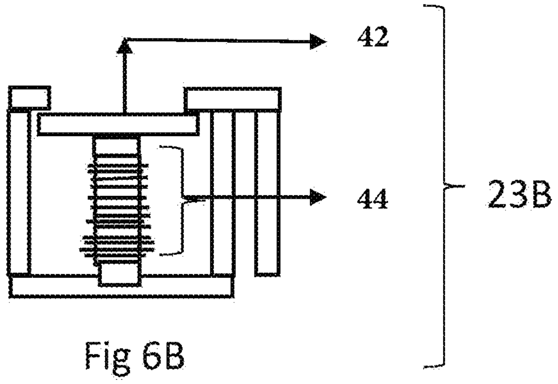
FIG. 6B illustrates the top-flanged cup of FIG. 6A with an outstretched spring fitted in the interior of the top-flanged cup.
Figure 6C:
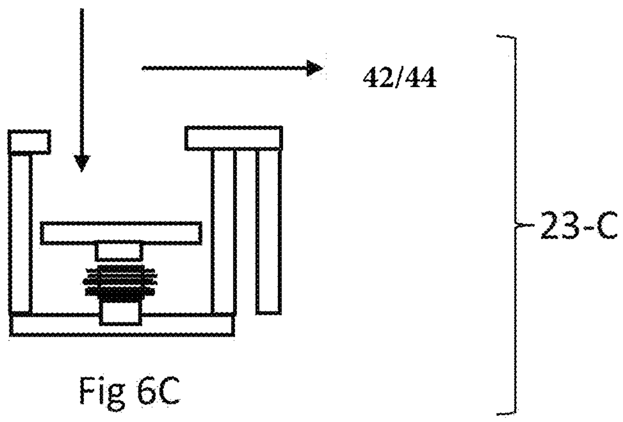
FIG. 6C illustrates the top-flanged cup of FIG. 6A with an outstretched spring fitted in the interior of the top-flanged cup in a compressed position.
Figure 6D:
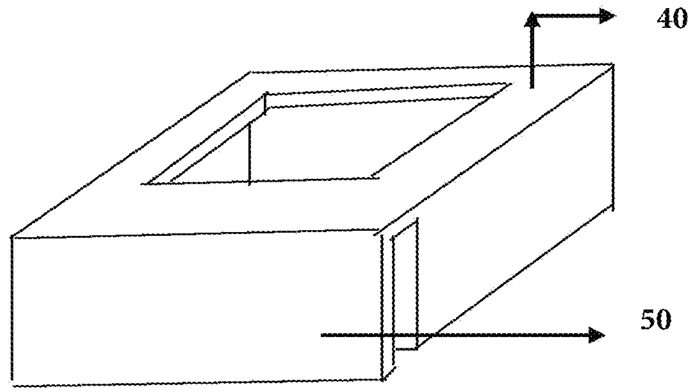
FIG. 6D illustrates a three dimensional exemplary view of a top-flanged cup as shown in FIG. 6A from a front side.
Figure 6E:
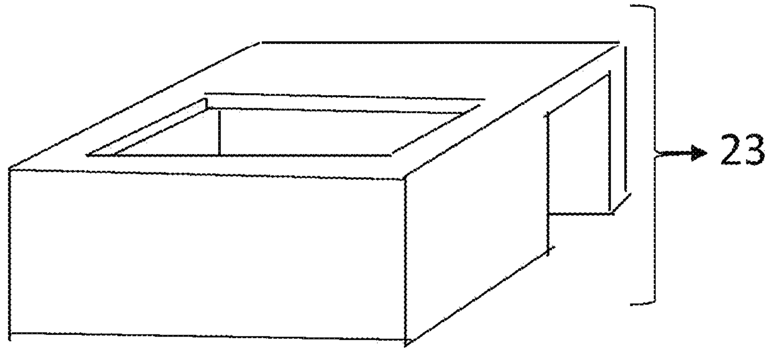
FIG. 6E illustrates a three dimensional exemplary view of a top-flanged cup as shown in FIG. 6A from a back side.

FIG. 6A, FIG. 6B, and FIG. 6C show cross-sectional side views of the top-flanged cup 23. The top-flanged cup 23 in FIG. 6A is shown without the interior spring 44. The top-flanged cup 23 is also shown in FIG. 6B with the interior spring 44 fitted in place in an expanded position. FIG. 6C shows the device top-flanged cup 23 with top-flanged cup holder 50; out-stretched spring 44 fitted to the interior center base 46 of the bottom part 48 of the top-flanged cup; further, top part of the out-stretched spring suspends a flat-plate 42 that may freely move in the cup but restricted by the cup flange 40.

FIG. 6. (23C) illustrates a cross-sectional side view of exemplary device top-flanged cup (23) with Out-stretched spring 44 compressed due to pressing down of the flat-plate 42. More so, FIGS. 6.(D & E) illustrated and exemplary three-dimensional appearance of top-flanged cup.

Figure 7A:
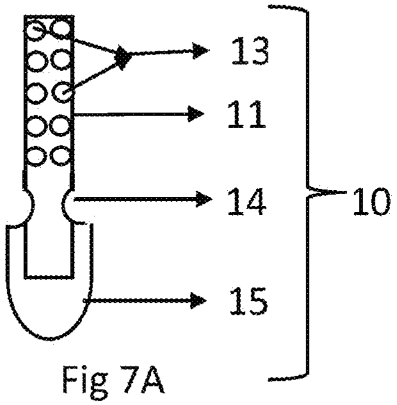
FIG. 7A illustrates an exemplary view of a modified dispenser cartridge having an inbuilt perforated funnel packed absorbent embedded into a flat brim semi-oval shaped cup.
Figure 7B:
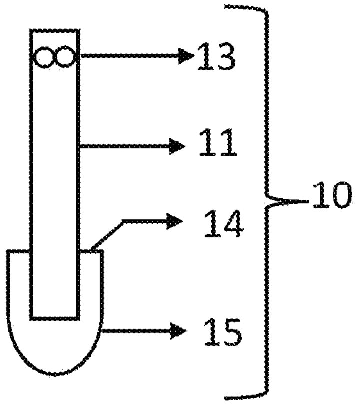
FIG. 7B illustrates an exemplary view of a modified dispenser cartridge having an inbuilt perforated funnel packed absorbent in a semi-oval shaped cup.
Figure 7C:
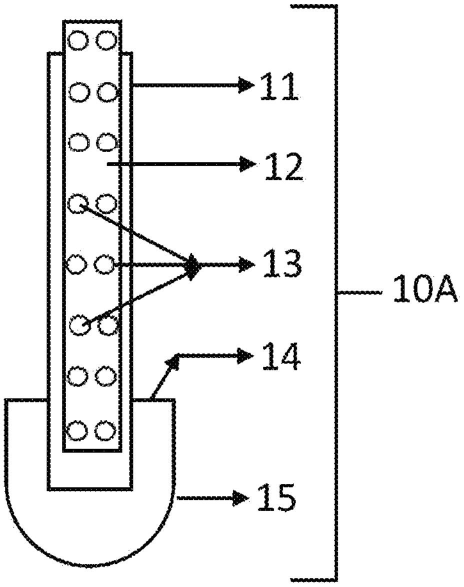
FIG. 7C illustrates an exemplary view of an absorbent stick in a semi-oval shaped cup.

FIG. 7. Illustrated cross sectional view of exemplary embodiment of modified dispenser cartridge comprises of cylindrical, cubic, or cuboid container, etc 11 embedded into solid thick flat-brim 14 semi-oval shaped cup 15. A fluid filled cartridge may have an inbuilt perforated 13 funnel-packed absorbent or a stick of absorbent 12 that may extend out of the container to facilitate fluid to evaporate out of the fluid container.

Figure 8A:
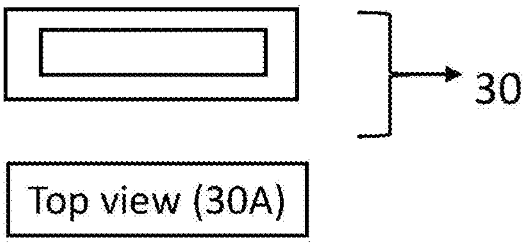
FIG. 8A illustrates a top view of a surface affixable cup holder.
Figure 8B:
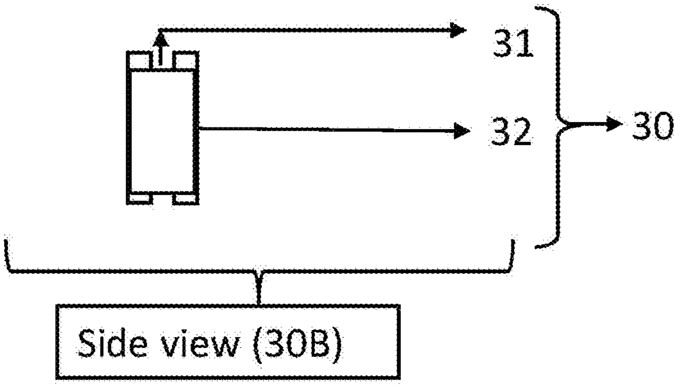
FIG. 8B illustrates a side view of a surface affixable cup holder.
Figure 8C:
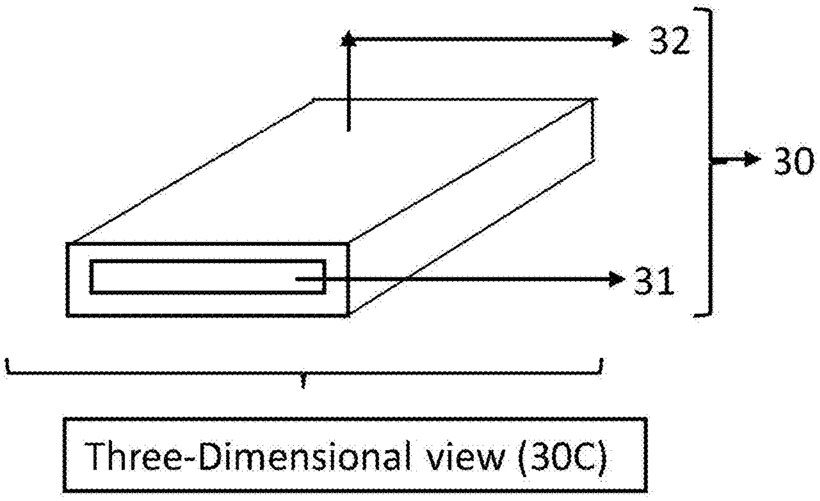
FIG. 8C illustrates a three dimensional view of the surface affixable cup holder of FIG. 8A.

FIG. 8. sub-figures. illustrates a cross-sectional top view 30A FIG. 8A; side view 30B FIG. 8B; and three-dimensional view 30C FIG. 8C of exemplary embodiments of the surface affixable cup holder.

Figure 9:
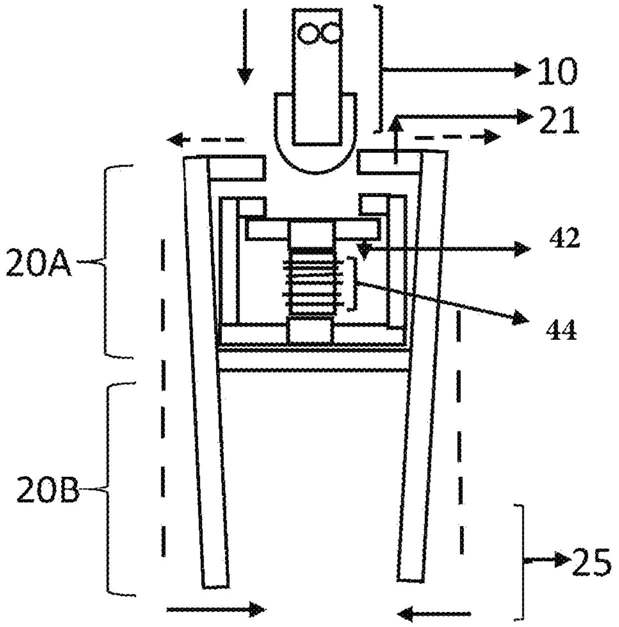
FIG. 9 illustrates a cross-sectional side view of exemplary device thumb-finger compression by the lower "H" shaped arms of the air disinfectant holder-ejector device causing the upper "H" shaped arms to pull back for insertion of the oval-base air disinfectant cartridge.

FIG. 9. illustrates a cross-sectional side view of exemplary device thumb-finger compression by the lower "H" shaped arm 20B/25 of the device causing the upper "H" shaped arm 20A to pull back for insertion of the oval-base cartridge 10.

Figure 10:
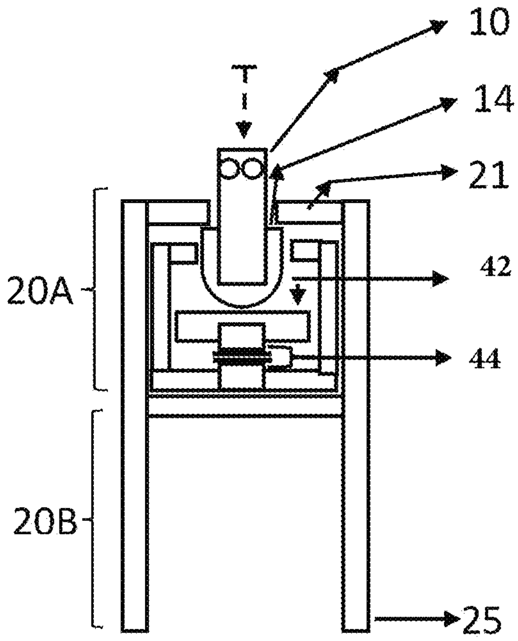
FIG. 10 illustrates a cross-sectional side view of exemplary device thumb-finger release of the lower "H" shaped arms of the device causing the upper "H" shaped arms to return to rest and the device stoppers resting against a surface of the air disinfectant cartridge with the spring under compression.

FIG. 10. illustrates cross-sectional side view of exemplary device thumb-finger release of the lower "H" shaped arm 20B/25 of the device causing the upper "H" shaped arm 20A to return to rest securing cartridge by device stoppers 21 resting against cartridge flat-brim/grippable surface 14. Further, as shown in FIG. 10, cartridge insertion causes suspended flat-plate depression and out-stretched spring compression.

Figure 11:
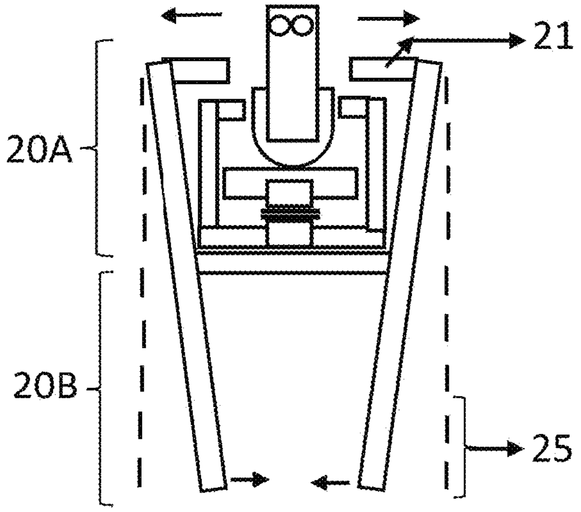
FIG. 11 illustrates a cross-sectional side view of exemplary device thumb-finger compression of lower "H" shaped-arms causing the upper "H" shaped arms to pull back, causing disengagement from the device cartridge.

FIG. 11. illustrates a cross-sectional side view of exemplary device thumb-finger compression of lower "H" shaped-arm 20B/25 causing upper "H" shaped arm 20A to pull back, device stopper 21 disengagement from cartridge flat-brim top 14.

Figure 12:
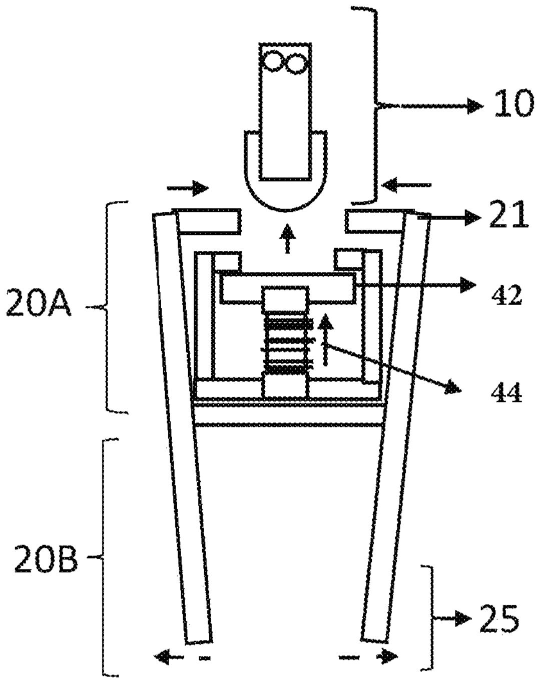
FIG. 12 illustrates a cross-sectional frontal view of the device showing thumb-finger compression by the lower "H" shaped arms of the device causing expansion of out-stretched spring with a flat-plate rising, and the upward thrust of the air disinfectant cartridge.

FIG. 12. illustrates a cross-sectional frontal view of exemplary embodiments of the device thumb-finger compression by the lower "H" shaped arm 20B/25 of the device causing re-expansion of out-stretched spring 44, flat-plate 42 rising, and upward thrust of cartridge.

Figure 13:
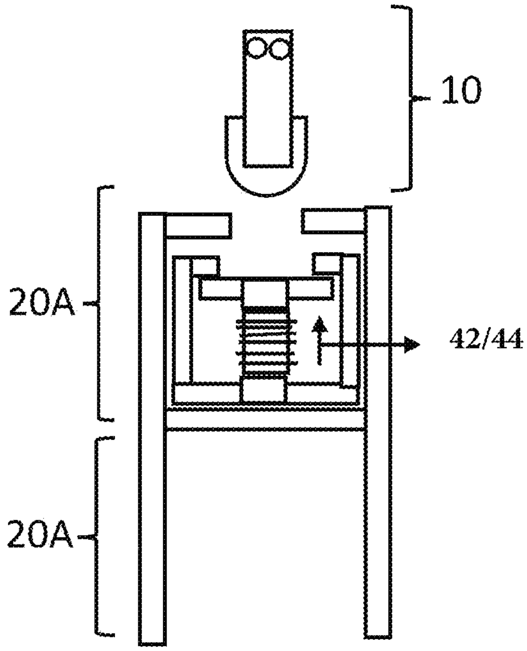
FIG. 13 illustrates a cross-sectional frontal view of the device at complete rest state; re-expansion of out-stretched spring, and flat-plate suspension at elevated level restricted by cup flange.

FIG. 13. illustrates a cross-sectional frontal view of exemplary embodiments of the device at complete rest state; re-expansion of out-stretched spring; and with the flat-plate suspension at elevated level restricted by cup flange.

Figure 14A:
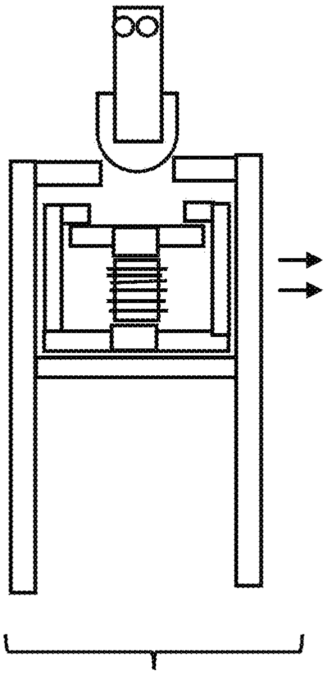
FIG. 14A shows a front view of the device having a top-flanged cup holder.
Figure 14B:
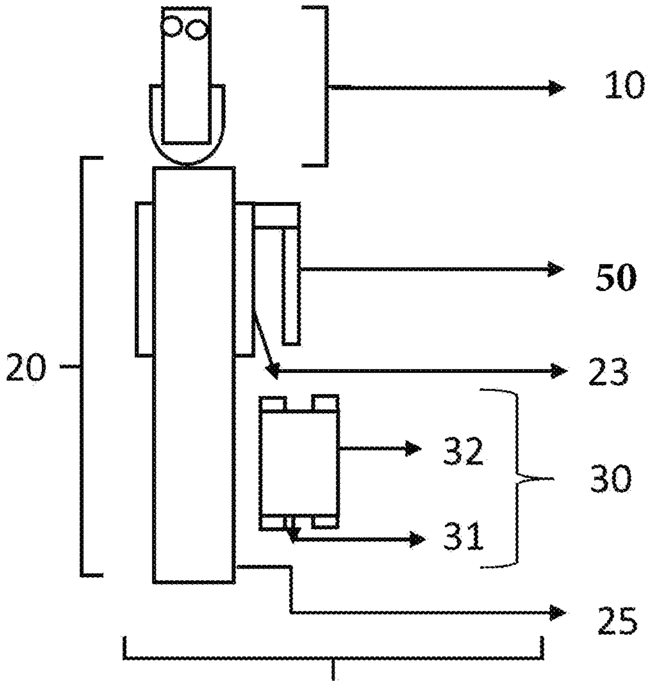
FIG. 14B shows a side view of the device having a top-flanged cup holder and a surface affixable cup holder and air disinfectant cartridge.

FIG. 14. Illustrates the exemplary embodiments of a cross-sectional frontal view 10/20 of the device 20, a cross-sectional side view 10/20/50/31 of same device 20 with device components: top-flanged cup holder 50 and surface affixable cup holder 30, and air freshener cartridge 10. It is recommended that the surface affixable cup holder is mounted to the desired surface prior to insertion of top-flanged cup holder into surface affixer.

Figure 15A:
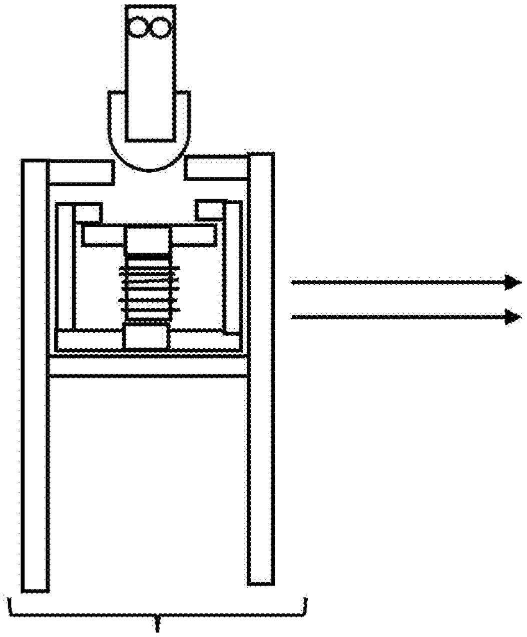
FIG. 15A shows a front view of the device.
Figure 15B:
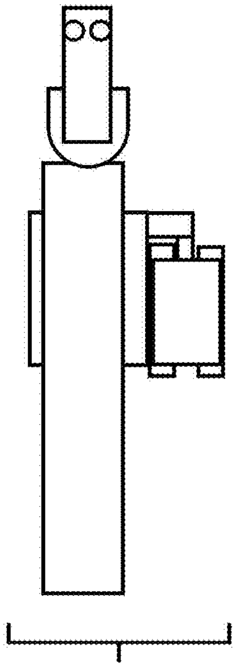
FIG. 15B shows a side view of the device having a top-flanged cup holder inserted into surface affixable cup holder.

FIG. 15. illustrates a cross-sectional frontal view, and cross-sectional side view of exemplary embodiments of the device top-flanged cup holder inserted into surface affixable cup holder.

Figure 16:
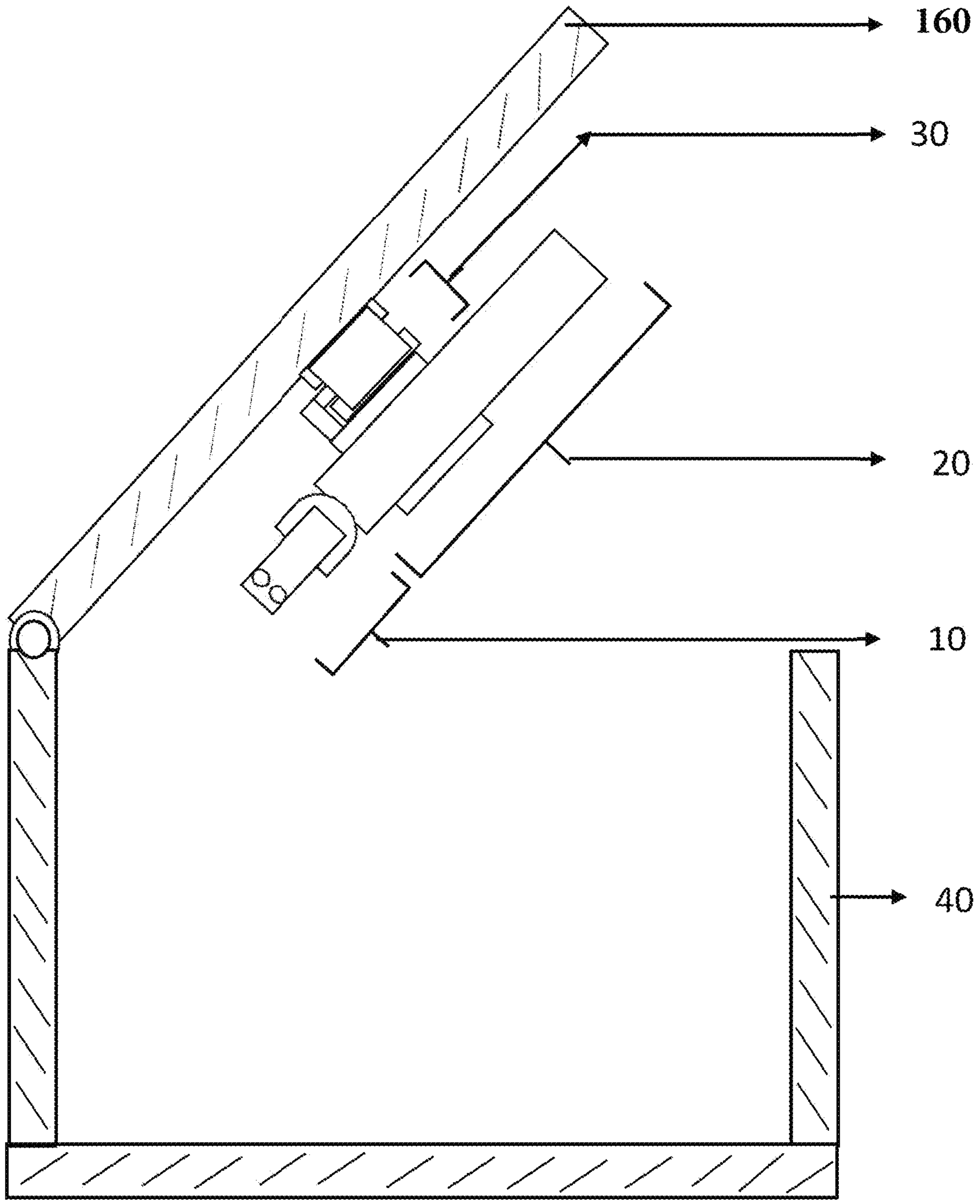
FIG. 16 illustrates a cross-sectional side view of exemplary embodiments of the surface mount air-freshener holder-ejector device mounted upside-down position into surface affixable cup holder that is installed via adhesive compound onto the lead cover of an enclosable unit.

FIG. 16. illustrates a cross-sectional side view of exemplary embodiments of the surface mount air-freshener holder-ejector device 20 mounted upside-down position into surface affixable cup holder 30 that is installed via adhesive compound onto the lead cover 160 of an enclosable unit 40 such as trash-can.

Surface mount air disinfectant/deodorizer holder-ejector device 20 with modified fluid container-dispenser adaptable to surface mount air disinfectant/deodorizer holder-ejector device (10), and affixable holder 30.

In various embodiment, cartridge may be disposable or refillable non-disposable unit and can be liquid filled or vaporizable solid fill with product finish identifier. As shown in FIG. 7, cartridge comprises of cylindrical, cubic, or cuboid container 11 embedded into solid thick flat-brim 14 oval shaped base cup 15. A fluid filled cartridge may have an inbuilt perforated 13 funnel-packed absorbent or a stick of absorbent 12 extending out of the container to facilitate fluid to evaporate out of the fluid container.

As shown in FIG. 7, a solid evaporator filled cartridge 10 may have perforations 13 at the opposite end of the semi-enclosing solid cup. Perforations will allow evaporation of solid deodorizer, disinfectant, or repellant into an enclosed environment. A finish identifier in a form of color-coding to alert content finish may be included.

Figure 3A:
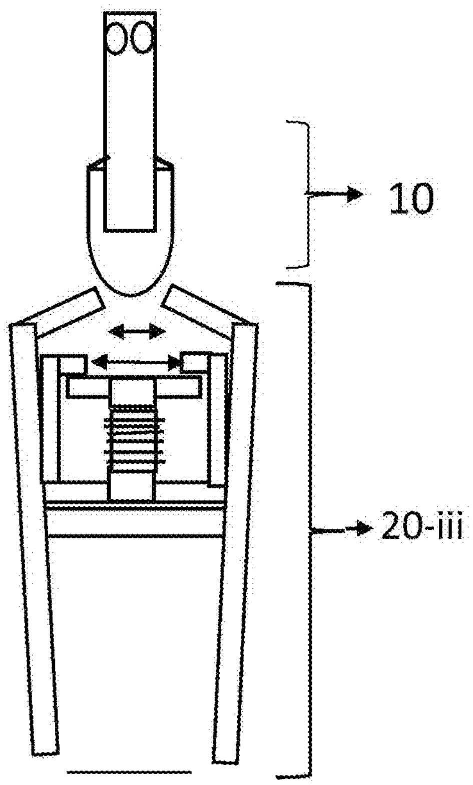
FIG. 3A shows another embodiment of the air disinfectant cartridge being inserted into the air disinfectant holder-ejector device with the stopper arms partially raised.
Figure 3B:
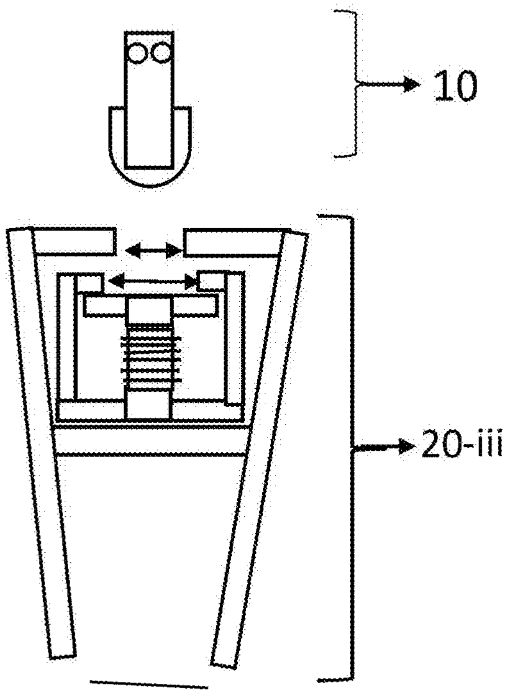
FIG. 3B shows the embodiment of the air disinfectant cartridge shown in FIG. 3A being inserted into the device with the stopper arms closed.

In this embodiments, air disinfectant/deodorizer holder-ejector device 20 may take the appearance of letter "H"; inward slanted upper arm of letter "H"; inward slanted lower arm of letter "H"; or slightly curved bilateral arms of letter "H", as illustrated in FIGS. 1, 2, 3, & their respective sub-figures. As shown in the afore mentioned illustrations, the upper "H" arms 20A of the device may have inward projection forming stopper ends 21 or sawtooth grippable inner surface of the end of the upper "H" arm 20A of the device. The lower "H" arm 20B of the device may be thumb-finger compressible ends 25 that will result in the outward extension (pulling back) of the upper arm along with stopper ends 20A/21 away from the center 22 as shown in FIG. 4, FIG. 9, and FIG. 11.

As illustrated in FIG. 1, a cross-sectional side view, and in FIG. 5, a three dimensional-sectional view of exemplary embodiments of the device, a flanged top cup 23 tightly fitted on horizontal beam 24 connecting both arms of the device as in vertical "H" shaped arms of the letter "H". As shown in FIG. 6., an inverted letter "L" shaped cup holder 50 located on the cup-side surface that is perpendicular to side surface location of letter "H" shaped a rms of the device. The top-flanged cup holder 50 (23 ii) dimensions may be penetrable to hallo space 31 of the surface affixable cup holder 30, securely fit in surface affixer, and can be remove with ease.

In various embodiment, as shown in FIGS. 6(B & C), out-stretched spring 44 secured to the base 46 of the top-flanged cup firmly suspends a flat-plate 42. As illustrated in various figures, the flat-plate is of same shape as the internal shape of the top-flanged cup and rests against the cup flange 40 with pressure. As illustrated in FIGS. 6(B & C) of the cross-sectional front views of exemplary embodiments of the device, the movement of spring suspended flat-plate is free within the top-flanged cup except restriction by the flange.

The skilled artisan will appreciate that while the depth of the device top-flanged cup accommodates spring-plate compression and a proportional length of the cartridge, the cup flange does not restrict the cartridge insertion and the ejection movement processes.

FIG. 8. illustrates removable or non-removable surface affixable cup holder (30) that has two surfaces (32) and a central hallo (31) same shape and dimensions as the cup holder 50. In various embodiment, the surface affixable cup holder can be mounted via adhesive compound to any desired surface or on the internal surface of the enclosed unit. The top-flange cup holder 50 of the device may easily slide into the hallo aspect (31) of the affixable cup holder and remained secure.

In various embodiments, the cartridge may be place into the device by thumb-finger compression of the lower "H" shaped arms (20B/25) causing the upper "H" shaped arm (20A) to pull outward along with the stopper (21) to allow placement of cartridge by semi-oval base (15) into device cup (23). Insertion force of cartridge by semi-oval base causes spring suspended flat-plate 42 to compress the spring 44. Upper "H" shaped arm of the device (20A) returns to rest along with both stoppers (21) resting on the flat-brim top (14) of solid cup base of the cartridge, thereby countering spring-plate opposing outward pressure.

As illustrated in FIGS. 11& 12 cross-sectional front view of exemplary embodiments of the device, cartridge ejection operation begins by thumb-finger compression of the lower "H" shaped arms (20B/25) of the device causing simultaneous outward pull of the upper "H" shaped arms (20A) and stoppers (21). Subsequently allowing the spring 44 to stretch out pushing the flat-plate 42 to ejecting cartridge out of the device cup (23). As illustrated in FIG. 13., removal of thumb-finger compression causes upper (20A) and lower (20B) "H" shaped arms of the device to returns to rest. It is generally desirable to install the device upside-down on the internal cover of the trash-can, as an example, so that cartridge ejection will direct the cartridge into the trash-can.

It is to be understood that the above description is intended to be illustrative, and not restrictive. Many other embodiments will be apparent to those skilled in the art, upon reviewing the above description. The scope of the invention should, therefore, be determined with reference to any appended claims, along with the full scope of equivalents to which such claims are entitled.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set. Also, as used herein, the terms "has," "have," "having," or the like are intended to be open-ended terms.

The presence or absence of a summary, abstract, or claims in this application should in no way be considered as limiting on the scope of any inventions disclosed herein.

What is claimed is:

1. A device, comprising:

an air disinfectant/deodorizer device having a cartridge for deodorizing or disinfecting a trash can, comprising:

a body wherein the body takes appearance of the letter "H" shape that is thumb-finger grip fitted with encased holder-ejector unit mounted on a horizontal arm of the device as on a horizontal arm of a letter "H".

2. The device of claim 1, wherein the device is in the resemblance of the letter "H" shape having an inward slanted upper arm of the letter "H" shape and an inward slanted lower arm of the letter "H" shape or a slightly curve bilateral arms of the letter "H" shape.

3. The device of claim 1, wherein a holder-ejector unit is mounted on a horizontal arm of the device such that holder-ejector component of the device comprises a top-flanged cup, a spring fitted to an interior center base of the top-flanged cup, and a free movable flat-plate suspended to the opposite end of the spring, and the flat-plate is configured to be restricted by a flange of an encasement, wherein the spring is configured to be outstretched or compressed.

4. The device of claim 3, wherein the device further comprises, the spring fitted in the interior base of the top-flanged cup of the holder-ejector unit mounted on the horizontal arm device, wherein an opposite end of the spring suspends the free movable flat-plate that can freely move in the top-flanged cup of the device upon downward pressure but is at rest when restricted by the encasement flange.

5. The device of claim 1, wherein the ends of the two upper "H" shaped arms of the device have inward projection forming stoppers or grippable inner surface ends that substantially causes retention of removable cartridge when inside the encased holder-ejector unit.

6. The device of claim 1, wherein the two lower "H" shaped arms of the device are configured to be thumb-compressible and cause outward pull of the two upper "H" shaped arms of the device and the release of the two lower "H" shaped arms of the device will cause the two upper "H" shaped arms of the device to retract/return to original rest position.

7. The device of claim 1, wherein the cartridge is retained in the holder-ejector unit by means of stoppers/grip surface at ends of upper arms of the device.

* * * * *